United States Patent
Voneiff et al.

(10) Patent No.: US 7,600,457 B2
(45) Date of Patent: Oct. 13, 2009

(54) APPARATUS FOR AUTOMATICALLY PRODUCING TISSUE SLIDES

(76) Inventors: John Voneiff, 14 Blythewood Rd., Baltimore, MD (US) 21210; Jay Frederick Gibson, 8319 Catherine Ave., Pasadena, MD (US) 21122

( * ) Notice: Subject to any disclaimer, the term of this patent is extended or adjusted under 35 U.S.C. 154(b) by 272 days.

(21) Appl. No.: 10/091,173

(22) Filed: Mar. 6, 2002

(65) Prior Publication Data
US 2003/0022271 A1    Jan. 30, 2003

(51) Int. Cl.
B26D 3/00    (2006.01)
B26D 1/553   (2006.01)

(52) U.S. Cl. .................. 83/307.1; 83/651.1; 83/703; 83/915.5

(58) Field of Classification Search ........... 83/915.5, 83/651.1, 200.1, 307.1, 856, 857, 703; 435/40.52, 435/40.5; 700/247; 62/320
See application file for complete search history.

(56) References Cited

U.S. PATENT DOCUMENTS

| | | | | | |
|---|---|---|---|---|---|
| 3,286,575 | A | * | 11/1966 | Burkhardt | 83/915.5 |
| 3,552,247 | A | * | 1/1971 | Pickett | 83/915.5 |
| 3,667,330 | A | * | 6/1972 | Kobernick | 83/98 |
| 3,733,948 | A | * | 5/1973 | Pickett | 83/915.5 |
| 3,832,923 | A | * | 9/1974 | Lassmann et al. | 83/915.5 |
| 3,846,958 | A | * | 11/1974 | Divan | 83/367 |
| 4,505,175 | A | * | 3/1985 | Reichel | 83/703 |
| 4,548,108 | A | * | 10/1985 | Dennis | 83/371 |
| 4,941,375 | A | * | 7/1990 | Kasper | 83/367 |
| 5,125,303 | A | * | 6/1992 | Hoyland | 83/360 |
| 5,156,019 | A | * | 10/1992 | McCormick | 83/915.5 |
| 5,566,600 | A | * | 10/1996 | Johnson et al. | 83/932 |
| 5,713,255 | A | * | 2/1998 | Izvozichikov et al. | 83/915.5 |
| 5,989,835 | A | * | 11/1999 | Dunlay et al. | 435/40.5 |
| 6,006,737 | A | * | 12/1999 | Hayashi et al. | 125/16.02 |
| 6,074,868 | A | * | 6/2000 | Blumenfeld | 435/6 |
| 6,387,653 | B1 | * | 5/2002 | Voneiff et al. | 435/40.52 |
| 6,416,959 | B1 | * | 7/2002 | Giuliano et al. | 435/7.2 |
| 6,520,061 | B2 | * | 2/2003 | Fukuta et al. | 83/307.2 |
| 6,568,307 | B1 | * | 5/2003 | Gunther et al. | 83/915.5 |
| 6,763,748 | B2 | * | 7/2004 | Wolcott et al. | 83/932 |
| 6,925,920 | B1 | * | 8/2005 | Borosic | 83/857 |
| 7,374,907 | B1 | * | 5/2008 | Voneiff et al. | 435/40.52 |

* cited by examiner

Primary Examiner—Jason Daniel Prone
(74) Attorney, Agent, or Firm—Hunton & Williams LLP

(57) ABSTRACT

An apparatus and method for producing tissue slides is disclosed. The apparatus includes a holding assembly for manipulating the sample block, a blade assembly for preparing a thin section from the sample block, and a transfer roller mechanism for transferring the thin section to a receiving medium. The apparatus further includes a controller that may track the sample block and thin section. The method includes the steps of first locating a sample embedded within a support medium, which may be paraffin or a similar medium. Next, the embedded sample is oriented in such a way that its working surface is presented. This orientation may entail determining the orientation of the embedded sample with respect to the blade that will produce the largest cross-sectional area. Next, a slice of the sample from said embedded sample is removed and subsequently transferred to a suitable receiving medium, which may include a microscope slide.

4 Claims, 6 Drawing Sheets

APPARATUS FOR AUTOMATICALLY PRODUCING TISSUE SLIDES

BACKGROUND OF THE INVENTION

1. Field of the Invention

The invention relates generally to the field of histology. In particular, the present invention is directed to an apparatus and method for automatically producing tissue slides.

2. Description of Related Art

Histology, the study of the groups of tissues found in most multicellular plants and animals, often requires that the plant or animal tissue be provided in thin sections for study. One known technique to create thin sections of tissue is through the use of a microtome. The function of the microtome is simplistic and very much like that of any mechanical slicer which carves a pre-set measured slice and retains and advances that unit of measure for each subsequent cutting cycle. The cutting results are very much dependent upon a technician's practical skill.

Typically, tissue samples for general pathology examination are surrounded by a support medium and manually molded into standardized blocks. Paraffin is a known and commonly-used as a support medium. TissueTek O.C.T., manufactured by Sakura Finetek and available from VWR Scientific, West Chester, Pa., may also be used as a support medium. The optimum cutting temperature (O.C.T.) formulation of water-soluble glycols and resins in TissueTek O.C.T. provides a convenient specimen matrix for cryostat sectioning at temperatures of −10° C. and below. Resins and polymers, such as methacrylates, may also be used as support media. Although resins and polymers are primarily used for electron microscopy, they can also be used for standard microscopy with some adjustments for hardness of the final product. Suitable resins and polymers, including Araldite 502 Kit, Eponate 12™ Kit, and Glycol Methacrylate (GMA) Kit, are available from Ted Pella, Inc., Redding, Calif.

The tissue sample is manipulated in a metal support medium block mold by the technician so as to locate it close to what will become the top center surface of the support medium block. This top surface then becomes the working surface of the sample block. The sample block preparation process will be described using paraffin as the support medium.

As the tissue sample is being located and set within the support medium block mold, melted paraffin is added. The paraffin cools and hardens inside the block mold; and as it does, a plastic holder is inserted. In the hardening process, the bottom half of the paraffin block becomes locked within the frame of the plastic holder which becomes the base of the sample block. A technician then transfers the sample block to a microtome to prepare very thin sections of the tissue sample for later observation.

The prepared sample blocks are manually locked into an adjustable clamp assembly of the microtome. The technician can make limited manual adjustments to the clamp assembly in order to present the sample block's working surface to the microtome's cutting blade at an angle judged to be most favorable to yielding the best possible sample slice. The clamp adjustment for a given sample block is a subjective choice based on the judgement and experience of the technician.

The technician can make additional microtome adjustments that pre-set the starting lineal distance between the clamp assembly and the assembly holding the cutting blade, as well as the thickness of the sample slice each time the clamp assembly is cycled by moving it past the blade assembly. There is also limited adjustment of the angle of the cutting blade as presented to the clamp assembly; however, the optimum setting of the blade is typically about 45 degrees from vertical.

One sample slice is the product of one microtome cycle. Once a technician selects the orientation of the sample block's working surface to the cutting blade assembly's cutting blade, several cutting cycles are required to advance the cutting blade into the block to a working surface depth, where the slices then taken are suitable for slide application. These slices may be referred to as histologic grade slices, which are slices that a pathologist or other professional would find of acceptable quality for examination purposes. In particular, histologic grade slices are slices of a relatively uniform thickness without any significant tears, folds, wrinkles, or contamination from unrelated specimens or other artifacts. Histologic grade slices are substantially flat and smooth.

When a suitable sample depth is acquired, the technician may cycle the clamp (with the sample block locked within) one to several times to obtain a series of histologic grade slices. After each slice, a mechanism in the microtome advances the block toward the knife by the desired slice thickness, which may be set by the technician. A typical slice thickness is about 4 to 8 microns, but may vary from 1 to more than 10 microns.

The technician places the slices onto the surface of warm water, located in a pan next to the microtome. The tissue sample, still secured in its paraffin matrix, floats on the surface of the water. The warmth of the water softens the paraffin, thereby removing wrinkles or other distortions in the slice. The technician may also move a sample slice about on the surface of the water to facilitate this result.

Once the technician judges that the floating tissue/paraffin matrix sample has the desired flat form, the technician brings a receiving medium, such as a microscope slide, up under the portion of the floating sample slice that captures the full tissue specimen. Repetitive success in this, again, depends upon the skill of the technician. The slide with sample is then set aside for drying, staining and evaluation, or for various molecular or histochemical analysis.

Occasionally, such as during performance of surgical procedures, it may be necessary to get a rapid diagnosis of a pathologic process. For example, a surgeon may want to know if the margins of his resection for a malignant neoplasm are clear before closing, or an unexpected disease process may be found and require diagnosis to decide what to do next, or it may be necessary to determine if the appropriate tissue has been obtained for further workup of a disease process. This may accomplished through use of a frozen section.

Frozen sections are performed with an instrument called a cryostat. The cryostat is essentially a refrigerated box containing a microtome. The temperature inside the cryostat is about −20 to −30° C. The piece of tissue to be studied is snap frozen in a cold liquid or cold environment (−20 to −70° C.). TissueTek O.C.T. would be a suitable support medium for frozen sections. The freezing makes the tissue solid enough to section with a microtome. The tissue sections are cut and picked up on a glass slide. The sections are then ready for staining.

Although this process is effective, it is very time consuming and very dependent on the skill of the technician. As hospitals and laboratories seek to lower operating costs, they will seek to find more efficient ways to accomplish inefficient tasks. Also, it is desirable to reduce the variation in sample preparation that may occur between different technicians.

SUMMARY OF THE INVENTION

Therefore, a need has arisen for an improved apparatus and method for producing histological slides.

It is an object of the present invention to automatically perform the combined functions of the microtome and the technician.

It is a further object of the present invention to utilize mechanical robotic mechanisms to manipulate sample blocks and slides.

It is another object of the present invention to automatically determine the optimal working surface of the tissue sample.

A method of producing thin sections from an embedded sample is disclosed. In one embodiment, the method includes first locating a sample embedded within a support medium, which may be paraffin or a similar medium. Next, the embedded sample is oriented in such a way that its working surface is presented. This orientation may entail determining the orientation of the embedded sample with respect to the cutting blade that will produce the largest cross-sectional area. Next, a slice of the sample from said embedded sample is removed and subsequently transferred to a suitable receiving medium, which may include a microscope slide.

In another embodiment, an apparatus for applying thin sections of a tissue sample to a receiving medium is disclosed. The apparatus includes a slicing means for slicing thin sections from a tissue sample. The slicing means typically includes one or more cutting blades for slicing the tissue sample. The slicing means may include a first blade assembly that slices the tissue sample to expose the tissue sample's working surface, and a second blade assembly for producing thin sections of the tissue sample. The apparatus further includes a plurality of transfer rollers that are sequentially arranged in tangential proximity to each other, such that a thin section on the surface of one transfer roller will be transferred to the surface of the sequentially successive transfer roller. The first sequential transfer roller of is oriented in proximity to the slicing means so that a thin section sliced from said tissue sample contacts the surface of the first sequential transfer roller. A receiving medium is disposed in tangential proximity to a final sequential transfer roller, so that a thin section on the surface of the final sequential transfer roller will be transferred to the receiving medium in a substantially smooth and flat configuration.

In another embodiment, a method for applying thin sections of a tissue sample to a receiving medium is disclosed. The method includes first slicing a thin section from a tissue sample. The slicing causes the thin section to peel from the sample and adhere to a first transfer roller. Next, the thin section is transferred from the first transfer roller to an adjacent transfer roller that is in tangential proximity with the first transfer roller. Finally, the thin section is transferred from a final transfer roller to a receiving medium that is in tangential proximity with the final transfer roller. The thin section is placed on the receiving medium in a substantially smooth and flat configuration.

In another embodiment, an apparatus for automatically producing tissue slides from a tissue sample within a sample block is disclosed. The apparatus includes a holding assembly for manipulating the sample block, a blade assembly for preparing a thin section from the sample block, and a transfer roller mechanism for transferring the thin section to a receiving medium. The apparatus further includes a controller that may track the sample block and thin section.

Other objects, features, and advantages will be apparent to persons of ordinary skill in the art in view of the following detailed description of preferred embodiments and the accompanying drawings.

BRIEF DESCRIPTION OF THE DRAWINGS

For a more complete understanding of the present invention, the needs satisfied thereby, and the features and advantages thereof, reference now is made to the following descriptions taken in connection with the accompanying drawings in which.

DETAILED DESCRIPTION OF PREFERRED EMBODIMENTS

The present invention provides for automatically performing one or more functions of the microtome and the technician in the manual process for making histologic slides, starting with the picking up and taking charge of the sample block with its embedded tissue, to the finished sample slide set aside for drying and staining. The invention utilizes mechanical robotic mechanisms which permit automatic manipulation of sample blocks and slides, maintaining positive identification of the tissue samples and encoding slides, as well as the use of optical imaging technology to locate the tissue sample within the sample block. Optical imaging technology may also be used to assist in the placement of the sample slice on the slide. All of the manipulations may be operated and controlled by computer, inclusive of cataloguing sample blocks and finished slides. In toto, the system of the present invention will standardize the process (especially relative to quality and production speed) and improve the collection, storage and output of information relating to sample blocks and finished slides.

Preferred embodiments of the present invention and their advantages may be understood by referring to FIGS. 1-5, like numerals being used for like corresponding parts in the various drawings.

Figure 1A:
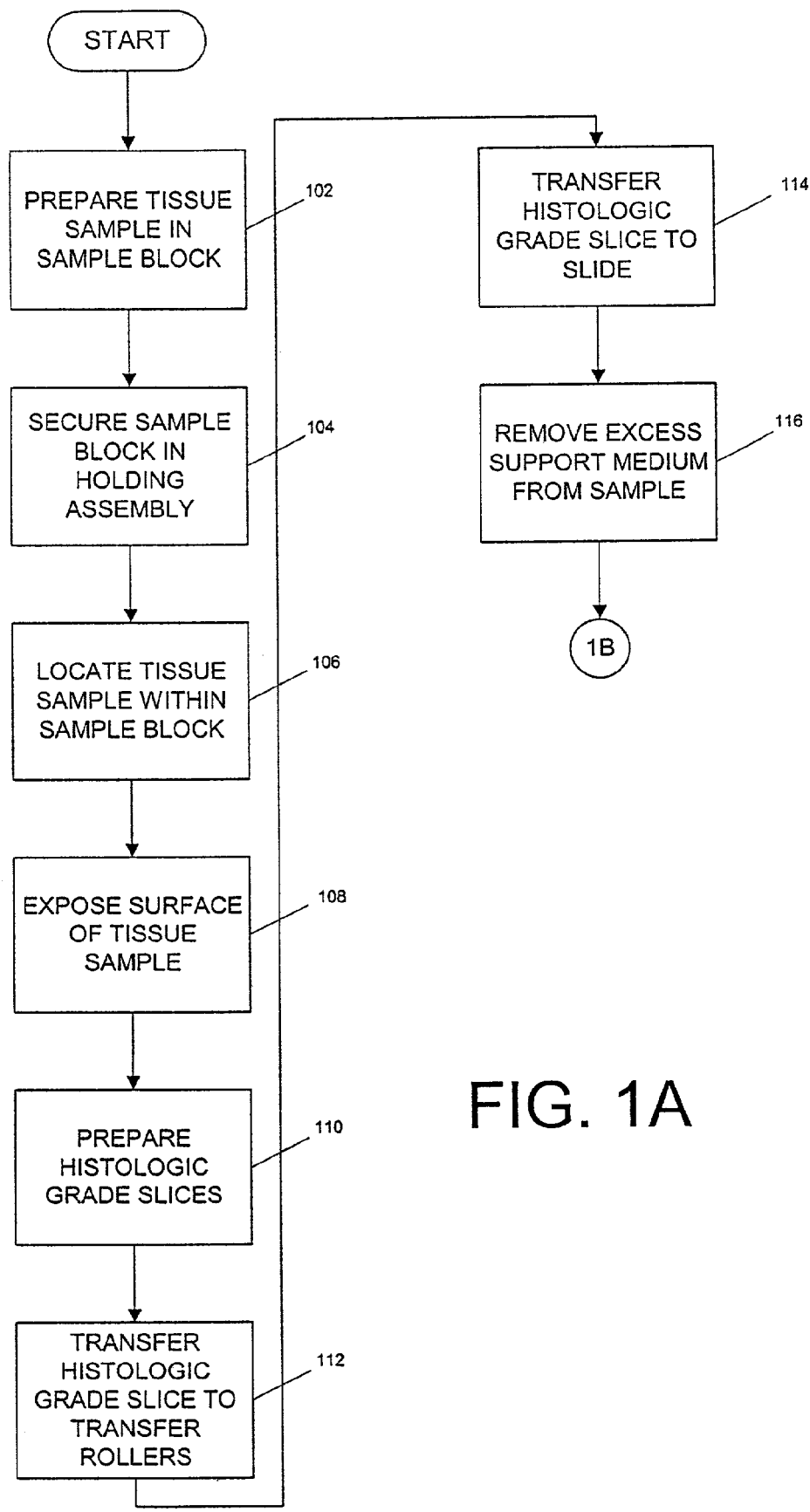
FIGS. 1a-b are a flowchart of a method for automatically producing tissue slides according to one embodiment of the present invention.
Figure 1B:
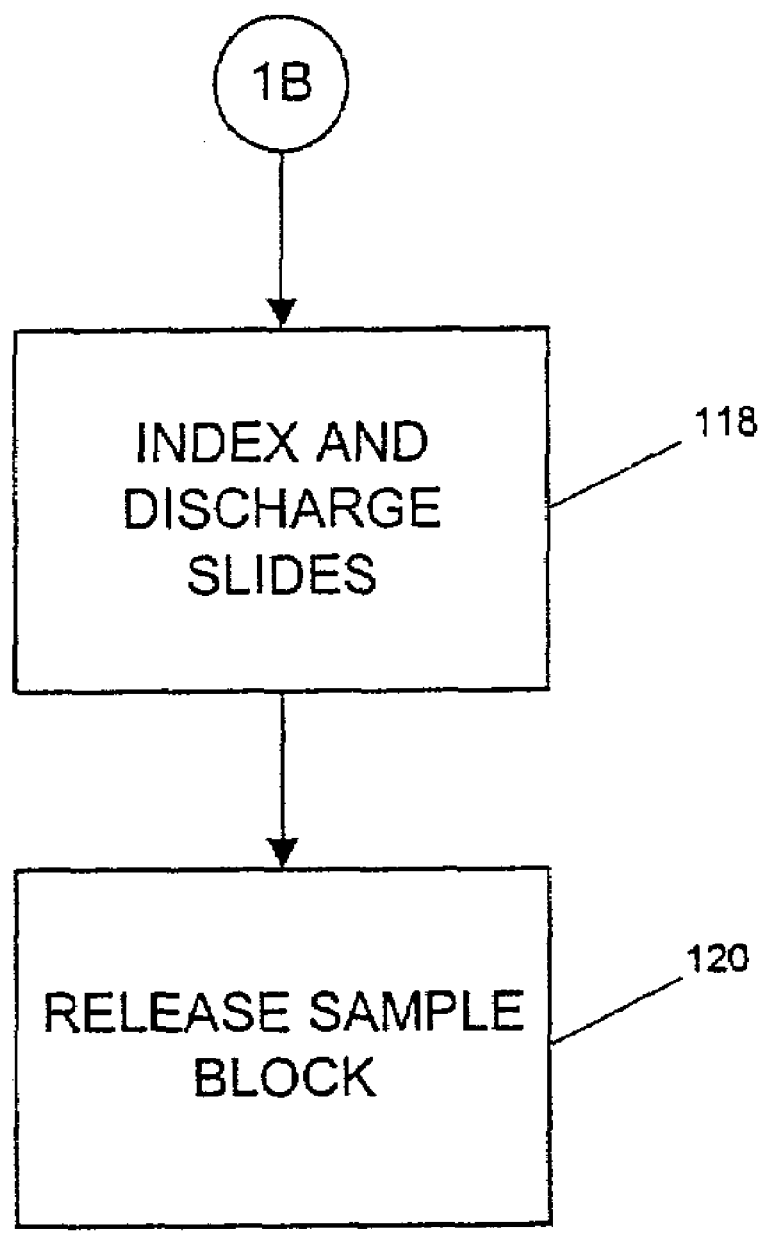

Referring to FIGS. 1a-b, a flowchart depicting the process of the present invention is provided. First, in step 102, a tissue sample is prepared. As used herein, the term "tissue" refers to a solid mass which is typically made up of biological cells, preferably from a human. However, the tissue is not limited to human tissue; it encompasses plant, animal, or any other tissue. The device of the present invention may also be used to create thin sections from samples of metals and other materials, so long as the hardness of the cutting blade exceeds the hardness of the material being cut.

The tissue sample may be any sample for which microscopic examination of thin sections is desirable. Procedures for collecting and handling such samples are well known in the art, and the sample may be prepared for sectioning by methods that are well-known in the art, such as by embedding the tissue sample in a suitable support medium, such as a standardized paraffin block, O.C.T., or resins and polymers, all discussed above.

The present invention will be discussed using paraffin as the support medium. The present invention, however, is not limited to using paraffin as the support medium. Any suitable support medium, including, but not limited to, the known support medium discussed above, may also be used. Within the contemplation of this invention, other support media may require minor variations in the method and apparatus of this invention which are within the skill in the art in view of the guidance provided herein.

The prepared sample block may labeled with information about the sample, such as, inter alia, tissue sample control numbers, type of tissue sample, etc. Known input and labeling equipment may be used to input the information and to prepare the labels. The technician preparing the tissue sample may input information regarding the patient's name, type of sample (i.e., what organ the sample came from), the number of slides that are to be made, clinical diagnosis, or any other relevant information, and may affix a label containing some or all of the information on the side or on the non-working surface of the sample. The information may be fixed to the block in machine-readable form. For example, this information may be provided in a scannable bar code. Other forms of storage, such as magnetic media, may also be used. Alternatively, a code affixed to the block may correlate with information about the sample stored external to the block, and the code may facilitate access to the information.

Preferably, a sample block's code must be read before it can be processed. In the event a code can not be read, then the processing sequence may be stopped automatically. The technician could then manually eject the sample block in question, or the system could be pre-set to automatically eject any sample blocks for which the code is in any way suspect. In another embodiment, the technician may be able to override the system and continue the process despite the sample block code error.

In step 104, the sample is loaded in a holding assembly. This may be done automatically, or it may be done manually. The holding assembly may secure the sample block with several prongs; other means of holding the sample may also be used.

In one embodiment, a robotic clamp is used as a holding assembly. The robotic clamp can move the sample through various processing stations during preparation of the thin sections for positioning on the slides. The robotic clamp may provide the ability to rotate the sample block in three dimensions, which results in the optimum orientation of the working surface of the tissue sample to the blade. In another embodiment, the robotic clamp may have the ability to rotate the block in two dimensions. The rotation may be in set increments; for example, in increments of 2 degree arcs. Other suitable increments may also be used.

In another embodiment, negative pressure (a vacuum) may be used to secure the sample. Because the sample blocks are generally of a standardized size, a vacuum clamp positioned on one side of the sample block may apply negative pressure. The sample block is then secured to the vacuum clamp as long as negative pressure is applied. Any other suitable holding devices may be used.

In step 106, the position of the tissue sample within the prepared sample block that is in the holding assembly is determined. In the manual process, the general angle of the tissue sample in the sample block is determined by the technician when the paraffin wax hardens. In order to achieve the best slice of the sample tissue, it is generally desirable to present the maximum surface area of the tissue sample to the blades. If a sample block contains multiple tissue samples, it is generally desirable to orient the sample block so that the tissue samples are all at the same approximate depth with respect to the blade.

Any device or method that determines the depth and general mount angle of the tissue sample may be used. In one embodiment, an optical imaging system is used. This may include optical scanning devices using, e.g., focused light beams or lasers. Other methods and devices for determining the location of the tissue sample, such as RF waves, sonar, radar waves, X-rays, magnetic resonance, interferometers, etc., may also be used. In one embodiment, the optical imaging system locates the position and orientation of the tissue sample in the sample block in sufficient detail to permit the system controller to determine the desired orientation of the sample relative to the blade. Once the sample is optically scanned, the resulting data may be sent to the system controller, which processes the data in order to determine the appropriate orientation of the sample block.

Additional sensors may also be provided before the sample block is presented to the blades. In one embodiment, a metal detector is provided which detects the presence of metal in the sample, which could damage the blade. If metal is detected, the device may either alert the technician, automatically stop, or both.

In step 108, portions of the oriented sample block are removed to expose the embedded tissue sample. To do this, in one embodiment, the holding assembly moves the sample block to a blade assembly. The holding assembly may then cycle over the blade assembly as many times as required to reach the depth of the tissue sample, as determined in step 106. Each time the holding assembly cycles across the blade assembly, the holding assembly may incrementally move closer to the blade, permitting the blade to cut a disposable slice. Alternately, the blade assembly may cycle over the sample block and may incrementally move closer to the tissue sample with each cycle. The sample slices acquired during this step are typically discarded, preferably to a biologically-safe holding area.

The blade of the blade assembly may be made of any material having adequate hardness to cut the sample. Typically, the blade will be made of hardened spring steel. Alternatively, a cutting wire of narrow gauge or carbon fiber may be used, or the blade may contain diamond edges, or the blade may be made of surgical stainless steel.

Although the term "blade" is used generally to describe the component responsible for actually making the slice, it is understood that other mechanisms, devices, or components that accomplish this function could be substituted where their equivalence is readily apparent to one of ordinary skill. For example, cutting wires fall within the meaning of the term "blade" as used herein.

The blade may be continuous or discontinuous. In one embodiment, a continuous blade is supplied in a blade supply canister, incrementally advanced during the operation, and stored on a blade take-up canister. The continuous blade may be continuous roll of any suitable blade material. The blade assembly may be driven by a blade supply motor.

The blade may be advanced at predetermined intervals, such as the number of slices the particular section of blade has made. In another embodiment, the blade may advance when the sample block is changed. Other suitable criteria may also be use in order to ensure that the blade produces histologic grade slices. The blade may be incrementally advanced automatically, or it may be done manually by the technician.

Blade stock is accordingly incrementally rewound on spindles in the blade take-up canister. When the blade stock runs out, the empty blade supply canister is replaced with a fresh blade supply canister, and the used blade is discarded.

In one embodiment, two or more blade assemblies may be provided. The first blade assembly may be used to make the initial "rough" slices to expose the tissue sample, and a second blade assembly may be provided make the actual histologic grade slice or section. Providing at least two blade assemblies reduces the overall wear on the blade that makes the histologic grade slice by reducing the number of slices that it is required to make. This increases the overall life of the blade and reduces the downtime for blade replacement. Additional blade assemblies may be provided as necessary, and the blades may be of similar or different materials.

In an alternate embodiment, steps 106 and 108 may be performed simultaneously. In this embodiment, the slices that are removed from the sample block and monitored by a sensor. Slices are removed until the sensor determines that a sufficient cross-sectional area of the tissue sample is included in each slice. After this determination is made, histological grade slices are then produced.

In step 110, histologic grade slices are produced from sample blocks that have been brought to the desired depth for producing histologic grade slices. In one embodiment, where multiple blade assemblies are provided, the holding assembly advances the sample block toward the final blade by a predetermined amount after each cycle, and a given or pre-set number of histologic grade slices are automatically taken from the sample block's working surface.

In step 112, the histologic grade slice taken from the sample block is then applied directly to a transfer roller mechanism. At least one transfer roller for "picking up" the histologic grade slice and transferring it to a slide is provided. The purpose of the transfer roller mechanism is to capture histologic grade slices from the blade assembly and convey them to slides while reorientating the slices. In a preferred embodiment, the slices are reoriented from a generally vertical position to a generally horizontal orientation. In the process, the slices are softened so that they flatten and then smoothly transfer to the slide. One of the functions of the transfer roller mechanism, therefore, is to simulate the effect of the warm water bath on a given sample slice. An attractive force, such as negative pressure (a vacuum), may be used to help capture the slices, and a repulsive force, such as positive pressure, may be used to help release sample slices from the transfer roller mechanism. Other forms of force, such as electrical, magnetic, electrostatic, and chemical forces, may be used to aid in creating the attractive or repulsive force between the slice and the surface of the transfer roller.

Figure 2:
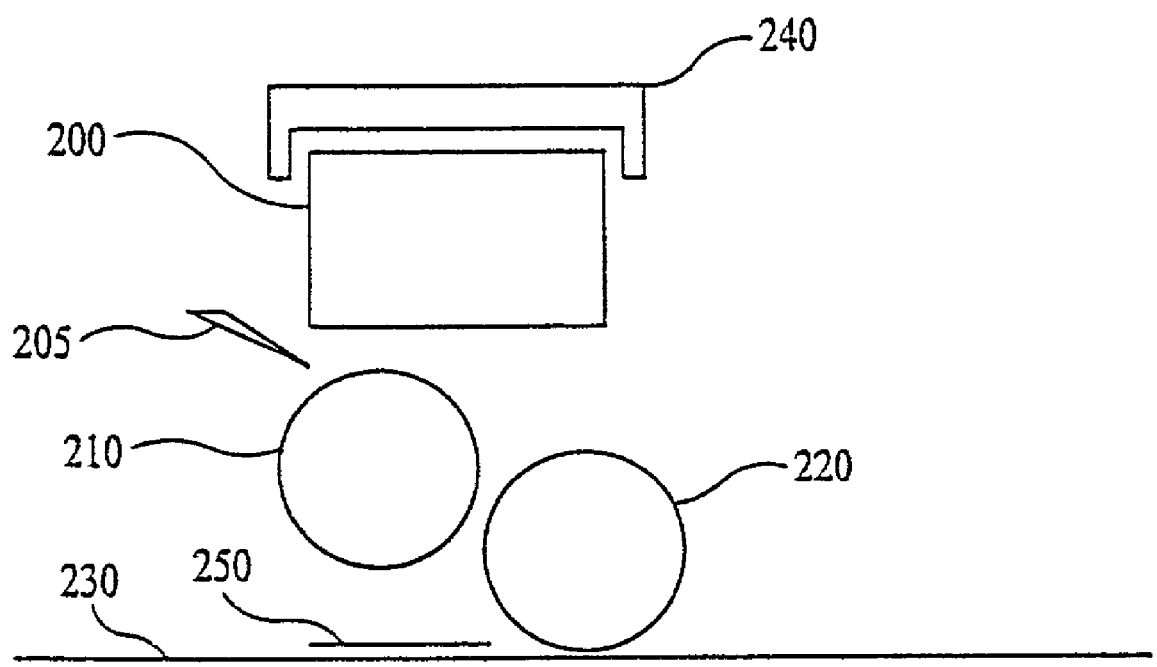
FIG. 2 schematic of the histologic grade slice blade and the transfer rollers according to one embodiment of the present invention.

In one embodiment, the transfer roller mechanism includes two transfer rollers 210 and 220. Such an embodiment is shown in FIG. 2. First transfer roller 210, which is located near second blade assembly 205, secures and takes control of a histologic grade slice (not shown) from sample block 200 as soon as that histologic grade slice begins to leave second blade assembly 205. To do this, the rotational speed of first transfer roller 210 may be set to match the linear motion of the holding assembly 240 relative to second blade assembly 205. Further, as discussed above, the transfer rollers can either generate an attractive force or can generate a repulsive force over a portion of their cylindrical surface, or over their entire cylindrical surface. This may depend upon the stage of rotation of the transfer roller. The application of an attractive force, which may be in the form of negative pressure, aids in picking up each histologic grade slice from second blade assembly 205, and also aids in spreading the slice smoothly in its longitudinal dimension. Finally, a repulsive force, which may be in the form of positive air pressure, can assist in the release, or transfer, of the histologic grade slice onto a subsequent transfer roller or onto slide 250 which may be located on slide conveyer 230.

Additional transfer rollers may be provided as necessary.

The surface of the transfer rollers may also be temperature controlled, including being heated or cooled. This temperature may vary depending on the support medium that surrounds the sample. In one embodiment, the surface of the transfer rollers are temperature controlled to a temperature sufficient to induce flattening of the support medium and tissue section. This temperature may be, for example, about 98° F.

Further, the transfer rollers may be coated with a non-stick material, such as titanium, urethane, Teflon™, nylon, or other suitable material. The surface of the transfer rollers may be porous, facilitating the adhesion, flattening, and release of the sample slice through the application of negative and positive pressure.

In an alternative embodiment, the sample slice is floated on a water surface as part of the process for smoothing the slice and transferring it to a slide. The slice may be received by the water surface directly from the blade and then picked up from the water by a transfer roller, or the transfer roller which receives the slice cut from the sample may place the slice onto the surface of the water. In either case, attractive and repulsive forces may assist as described above.

Referring again to FIG. 1, in step 114, the histologic grade slice is transferred to a suitable receiving medium, which may be a slide. The receiving medium will typically have at least one planar surface. In one embodiment, slides are fed from a slide dispenser and are printed to correspond to a given sample block and the number of slide samples required of that sample block. Once printed, the slides are advanced to the second transfer roller. In one embodiment, the slide is moved on a slide conveyor, which holds each slide independently of any other slide and in the process, cycles slides under the second transfer roller. The linear motion of the slide conveyor is timed to match the rotational speed of the second transfer roller, which, as discussed above, is also adjusted to match the rotational speed of the first transfer roller.

Minor adjustments to the slide may be made automatically as the slide approaches the final transfer roller. This may include automatic adjustments to the speed, positioning, and orientation of the slide, so that the histologic grade slice may be properly positioned on the slide. Additional sensors, including an optical imaging system, may be provided to determine the location of the sample slice relative to a slide and this information may be used to adjust the slide position. In another embodiment, manual adjustments may also be made by the technician.

In another embodiment, the slice may be secured in film or tape as the receiving medium. Suitable tape is disclosed in U.S. Pat. No. 5,746,855, which is hereby incorporated by reference in its entirety. In this embodiment, the sample may be transferred from the first or second transfer roller to the tape in a similar fashion as described above.

Prior to passing under the final transfer roller, the slide may be misted with distilled water. This misting wets the mounting surface of the slide to enhance the surface tension proprieties of both the slide and the histologic grade slice, forming a fluid bond between the surface of the slide and the surface of the histologic grade slice.

Other fluids may be misted on the surface of the slide. Generally, these fluids will have surface tension properties that permit a tissue slice in the support medium to adhere and spread on the surface of a slide without wrinkling, stretching, or tearing. The fluid will be selected from a group of fluids that will neither dissolve the tissue support medium nor the slide, nor will perceptibly distort the tissue slice or slide.

In an alternate embodiment, the surface of the histologic grade slice that will be in contact with the surface of the slide may be misted with a medium as described above.

In addition, the slide may be coded with information regarding the tissue sample. This information may include the information entered by the technician during the preparation of the sample block, and may further include information regarding the sample slice sequence where several sample slices are taken (e.g., "slice 7 of 20"). This information may be bar coded, and may be printed on the slide directly, or printed on a label and then affixed to the slide.

As the final transfer roller begins to interface with a slide, a repulsive force, such as controlled positive air pressure, may assist in the release of the histologic grade slice sample from the transfer roller onto the wet surface of the slide. The histologic grade slice adheres to the slide and moves beyond the transfer roller.

Following the transfer of the histologic grade slice to the slide, a pressure roller may be provided to apply light pressure to the sample on the slide to further flatten the histologic grade slice and to promote adhesion to the slide surface.

In optional step 116, any support medium that overhangs the slide may be removed. The slides may pass through the stripper assembly, which may have stripper fins that shift into contact with a slide, where a descending vertical motion against the edges the slide strips away, or trims, the support medium excess, with the excess being removed and automatically disposed of.

In step 118, the slides are discharged from the device. The slides then exit the device and may be either manually picked-up as they exit or an accumulating extension can be added to the exit conveyor to increase capacity. In one embodiment, the slides advance to the end of the slide conveyor and are then stacked 90 degrees incrementally onto the slide accumulation conveyor.

The finished slides may be conveyed to any other type of unit, such as a dryer, a stainer, image capture device or any other analytic device. The slide accumulation conveyor may have a final code scanner which checks the slide code sequence and automatically matches it with the sample block order of process and records it as complete.

Optionally, the technician may have the ability to manually over-ride the cycle of the slide accumulation conveyor. This ability will be useful at the end of a processing run where the technician wants to unload finished slides from the accumulation exit conveyor when there are no subsequent sample blocks to be processed.

In step 120, the sample block is released by the holding assembly. In one embodiment, the holding assembly moves the sample block to the discharge chute. The discharge chute can maintain the sample blocks in the order in which they were processed. The technician may be able to release the sample blocks by pressing a lever, or they may be automatically returned to a holding area.

The sample block chute optionally provides a biologically-safe and convenient means of disposal. The sample blocks may be released into a collecting device, which may be later retrieved by personnel for proper disposal.

Figure 3:
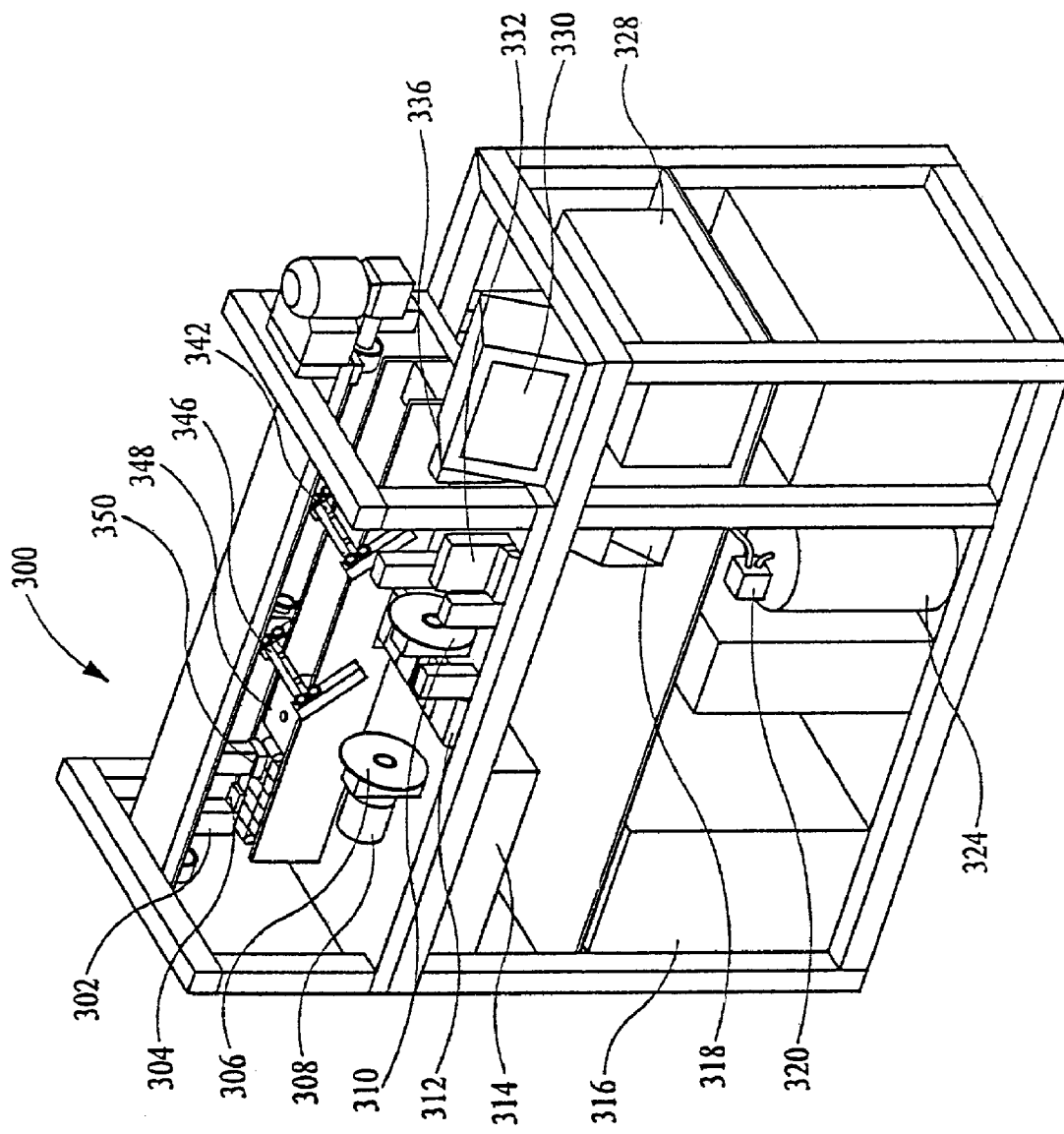
FIG. 3 is a perspective view of one embodiment of the present invention.
Figure 4:
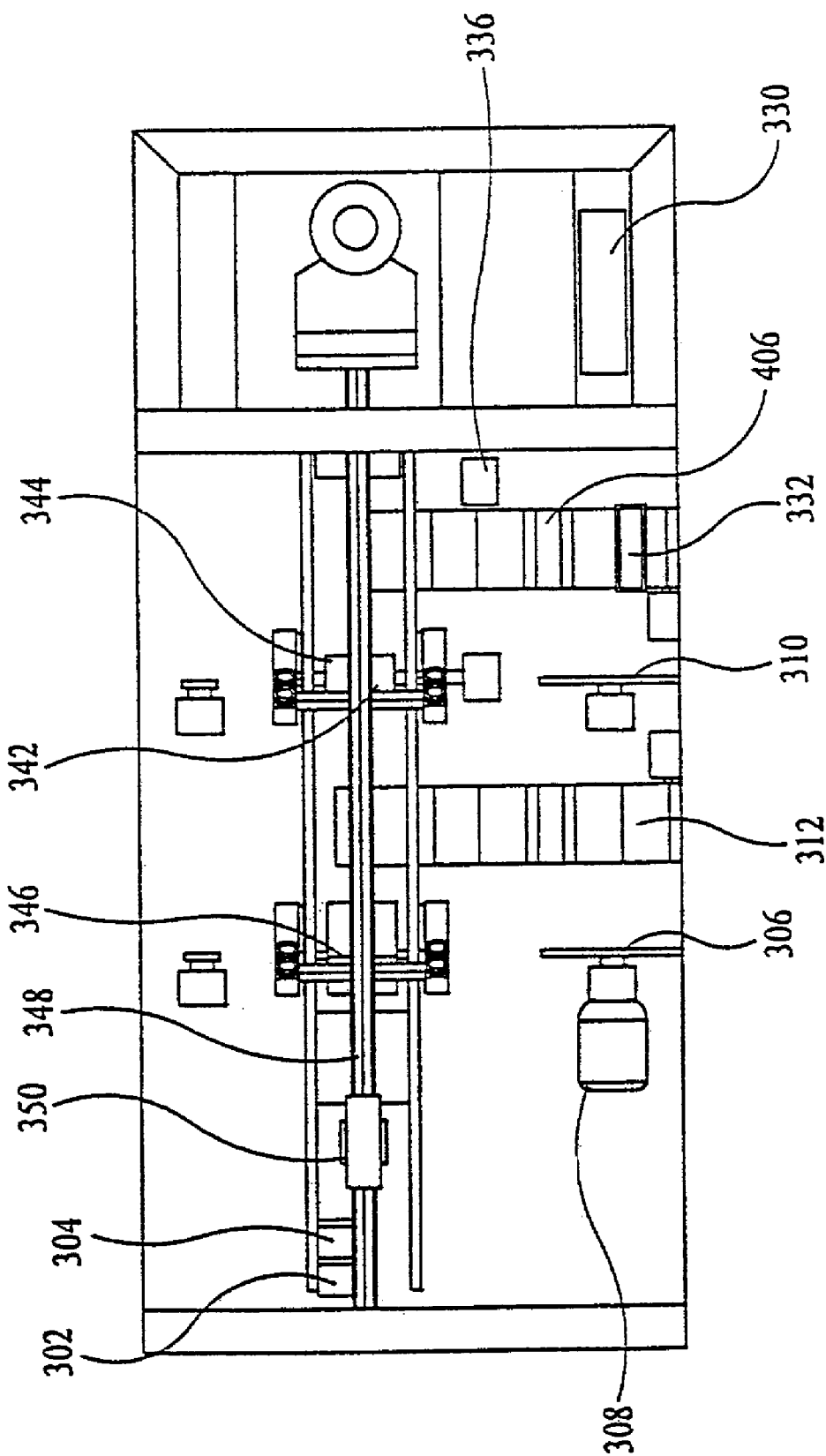
FIG. 4 is a top view of the embodiment shown in FIG. 3.
Figure 5:
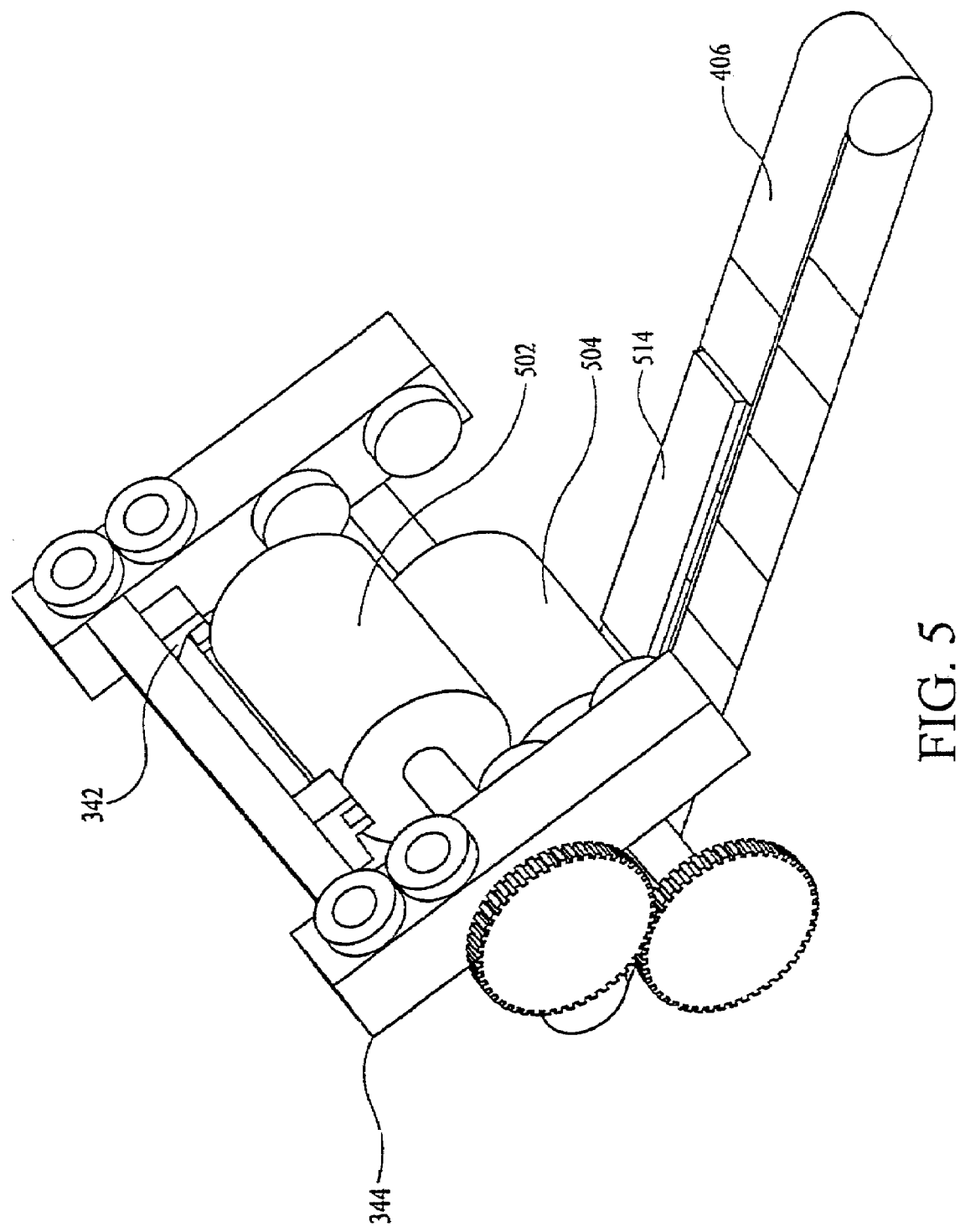
FIG. 5 is a perspective view of the transfer roller assembly of the embodiment shown in FIG. 3.

A preferred embodiment of the present invention is shown in FIGS. 3-5, which depicts the system for automatically producing tissue slides. System 300 is a preferred embodiment only, and the present invention is not limited to this preferred embodiment. The arrangement of elements of the system in FIGS. 3-5 in no way limits the present invention. It is within the contemplation of the present invention to arrange or modify elements of the system in accordance with other design requirements, such as, inter alia, the amount of space available to accomplish the method of this invention.

Referring to FIGS. 3 and 4, System 300 includes sample block loading area 302 and sample block identification area 304. In sample block loading area 302, sample blocks may be manually or automatically placed into a sample block dispenser (not shown). In the embodiment shown, the sample blocks are placed in sample block dispenser (not shown) such that their working surfaces are oriented downward. Sample block dispenser (not shown) may be positioned over a conveyor assembly for transferring the sample blocks to sample block identification area 304. As each sample block is added to the in-feed conveyor, its identification information is manually entered and stored in system controller 316, or the information may be automatically entered into the system controller by an optical scanner (not shown) that scans a pre-placed code on the sample block's plastic housing. This information may include, inter alia, patient's name, type of sample (i.e., what organ the sample came from), the number of slides that are to be made, clinical diagnosis, or any other relevant information.

System controller 316 may be any suitable microprocessor-based controller. In one embodiment, an Xpert 8 series computer, manufactured by Siemens AG, München, Germany, may be used as the controller. In another embodiment, a Scenic series computer, also manufactured by Siemens AG, may be used. In still another embodiment, a Pentium™-series microprocessor, manufactured by Intel, Inc., may be used.

The sample block code information may be displayed on display screen 330. Display screen 330 may be any suitable display means, including flat-panel displays, CRTs, LCD displays, and touch-screens. In one embodiment, a touch-screen is used to display information and to simultaneously serve as an input means. Other input means, such as keyboards, keypads, etc., may also be used. In one embodiment, SICOMP IMP 100, manufactured by Siemens AG, München, Germany, is used as a touch-screen display. Other suitable displays, including the MCM-series monitor, also available from Siemens AG, and other input means may also be used.

In one embodiment, display screen 330 may be used to display the progress of a particular sample block. Once the sample block is scanned, display screen 330 may present an image of the embedded tissue sample for the technician to view. This image may be presented in a perspective view, and the technician may be able to rotate the image. The intended depth of the slices may also be displayed.

Display screen 330 preferably also allows the technician to modify system parameters. For instance, the technician may have the ability to modify the temperature of either or both transfer rollers, the speed of the various conveyors, the oscillation speed and distance of the holding mechanism during slicing, etc.

Sample blocks may or may not include their own identification code. However, it is preferred that by the time a given sample block reaches the first processing station, its identification information and the sequence in which it was placed on the conveyor is registered in system controller 316. This information identifies products (slides), matches sequence number of the sample with codes related to the sample, and drives slide printer 328, which may be an ink jet printer, to print sample-related information on the slides. Thus, in the preferred embodiment, before the processing is initiated, system controller 316 matches the sequence number of the sample block about to undergo processing with the expected sample block's registered identification information.

After suitable identification of the sample block, the sample block is transferred to a first processing station. In the embodiment shown, the sample blocks are transferred by lug conveyor, which facilitates positive identification of the sample blocks.

At the first processing station, the sample blocks are secured by the holding assembly. In one embodiment, robotic clamp assembly 350 is used to secure the sample block. Robotic clamp assembly 350 may include traditional clamps, or may include vacuum clamps.

Robotic clamp 350 captures the leading sample block in queue. In one embodiment, robotic clamp 350 takes control of the sample block by grasping the length dimension sides of its plastic holder and moves it to a second processing station where it is scanned for tissue sample coordinates. In another embodiment, robotic clamp 350 uses negative pressure to secure the sample block.

Following clamping, the location of the tissue sample within the paraffin block is determined by optical imaging system 348. Optical imaging system 348 the depth and general mount angle of the tissue sample within the paraffin block portion of the sample block. Once the position of the tissue sample is established and entered into the system controller 316, robotic clamp 350 adjusts the paraffin block's working surface relative to blades at the next processing station to level the tissue sample and formulate its depth from the working surface of the surface of the paraffin block.

In a preferred embodiment, the robotic clamp assembly has the ability to, automatically adjust its position (and thereby the position of the sample block) to present the best orientation of paraffin block working surface to both of the blade assemblies further on in the process. In this process, target coordinates which identify the center of the tissue sample relative to the plane of the paraffin block's working surface are obtained based upon the located position of the tissue sample.

After determination of the location of the tissue sample at the second processing station, the sample block is moved to blade assemblies for cutting. In the embodiment shown, two blade assemblies for cutting into the sample block are provided: first blade assembly 346 for rough cutting to remove unwanted material from the tissue block; and second blade assembly 342 to produce histologic grade slices. Blades to cut the sample block are provided at each of these blade assemblies 346 and 342 by blade supply canisters 306 and 310, respectively. In the embodiment, blades (not shown) are several hundred inches long and are fed from the same type of canister and wound on the same type spindle. Blades (not shown) may be guided across their cutting assembly surfaces by a series of guide rollers (not shown).

The blades of first blade assembly 346 and second blade assembly 342 are each stored within the respective blade supply canisters, 306 and 310. The blade may be continuous roll of blade material. Further, both blade assemblies 346 and 342 may be driven by blade supply motor 308. A blade take-up canister may be provided for each blade supply canister 306 and 310 to received the used blade.

The blades may be any suitable cutting material. In one embodiment, hardened spring steel is used as a blade. Other blade materials, including carbon fiber, diamond edged strip, or surgical stainless steel, may alternatively be fed from blade supply canister 306 or 310 and wound into the respective take-up canister.

The blades of both first and second blade assemblies 346 and 342 may be incrementally advanced at predetermined intervals, as discussed above. For example, the blade may be advanced for each new sample block, or it may be advanced after a predetermined number of slices. In one embodiment, as soon as a sample block is sliced to tissue depth by first blade assembly 346, the blade in first blade assembly 346 may advance, and accordingly, as soon as histologic grade slices are produced at second blade assembly 342, the blade in second blade assembly 342 may also advance.

Blade stock is accordingly incrementally rewound on spindles in the blade take-up canisters (not shown). When either blade runs out, the empty blade supply canister is replaced with a fresh blade supply canister. The used blade is discarded. The blade canisters may be replacement items, with empty canisters being refilled and spindles also being reusable. The blade canister system provides for the easy disposal of medical waste. For instance, once the used blade is wound on the blade take-up canister, the blade take-up canister can be autoclaved and then discarded in the normal trash.

In another embodiment, standard fixed blades of a suitable material may be used. These materials may include the same materials used for the continuous blade. These fixed blades may be replaced automatically, or they may be replaced manually by the technician.

When the sample block is moved to first blade assembly 346, the angle of robotic clamp assembly 350 is automatically adjusted (guided by the input of the tissue sample coordinates) relative to first blade assembly 346. In one embodiment, robotic clamp 350 moves the sample block past first blade assembly 346 to cut the sample block. An equivalent mechanism in which first blade assembly 346 moves past a stationary sample block is also within the contemplation of this invention, as are embodiments where both first blade assembly 346 and sample block move in a coordinated fashion. Robotic clamp 350 may cycle, moving across first blade assembly 346 to cut successive slices from the sample block until the tissue sample is exposed and ready to yield useable histologic grade slices. Sample slices produced by these cycles fall onto accumulation exit conveyor 312 and are transported into paraffin scrap bin 314 for temporary storage and disposal.

Once the surface of the sample block has been cut to a desired depth for producing histologic grade slices in preparation for slicing, robotic clamp 350 is driven a pre-set distance to move the sample block to second blade assembly 342. Robotic clamp assembly 350 then automatically orientates to the same coordinates for a given sample block and moves to a position adjacent to blade assembly 342 where a given number of histologic grade slices are automatically taken from the paraffin block's working surface.

System controller 316 retains the information that enables the continuity of the slicing operation from first blade assembly 346 to second blade assembly 342. The difference is that slices taken at first blade assembly 346 are discarded into paraffin scrap bin 314, while slices taken at second blade assembly 342 are applied directly to first transfer roller 502 of transfer roller mechanism 344.

Transfer roller mechanism 344 is further shown in FIG. 5. First transfer roller 502 is positioned tangent to and above second transfer roller 504. Both first and second transfer rollers 502 and 504 may be coated with titanium, urethane, or other materials. Further, the surfaces of transfer rollers 502 and 504 may be coated with a porous material. As discussed above, both first and second transfer rollers 502 and 504 may have the ability to generate attractive and repulsive forces between the surface of the transfer roller and the slice, and may do this independently of each other and over all or a portion of the surface of each roller at any given time or position of rotation.

First transfer roller 502 is positioned directly below second blade assembly 342. First transfer roller 502 begins to pick-up and take control of a given histologic grade slice as soon as that slice begins to leave second blade 342. The rotational speed of first transfer roller 502 is timed to match the linear motion of robotic clamp 350 relative to second blade assembly 342.

First and second transfer rollers 502 and 504 are part of the mechanism that replicates the action of the technician's hand in pulling the histologic grade slice away from the blade and placing it in the water bath. First and second transfer rollers 502 and 504 replace the functions of moving histologic grade slices from the edge of the blade to the water bath and then from the water bath onto the empty slide.

Second transfer roller 504 is positioned tangent to and below transfer roller 502. The purpose of second transfer roller 504 is to be the interface between first transfer roller 502 and the slides. In the process, the tissue sample is inverted, further smoothed, located and applied to a corresponding slide.

Slide 514, or other suitable receiving medium, is fed from slide dispenser 332 and is printed to correspond to a given sample block and the number of slide samples required of that sample block. Once printed, slides are incrementally advanced on slide conveyor 406 which holds each slide independently of any other slide, and in the process, cycles coded slides under second transfer roller 504. The linear motion of slide conveyor 406 is timed to match the rotational speed of second transfer roller 504 which in turn is automatically adjustable to match the rotational speed of first transfer roller 502. As second transfer roller 504 begins its interface with slide 514, a repulsive force, which may be in the form of controlled positive pressure, aids the release of the tissue sample from second transfer roller 504 to slide 514's surface.

Referring again to FIG. 3, sprayer head 336, sprayer pump 320 and spray tank 324 are provided to mist the incoming slide with distilled water, or any other suitable material, to enhance the bonding between the histologic grade slice and slide 514.

Optionally, an optical scanner (not shown) focused on second transfer roller 504 verifies the location of the tissue sample by measuring its calibrated transverse and circumference center point coordinate sites. This information is input to system controller 316 to transversely adjust the entry of slide 514 relative to second transfer roller 504 and then control the timed release of the sample slice to slide 514. Second transfer roller 504 delivers the sample slice to slide 514. An exhaust of low pressure filtered air may assist in this transition. The transition position of slide 514 is controlled and based on the predetermined location of the center of the tissue sample on first transfer roller 502 and/or second transfer roller 504. Preferably, only one sample slice is on any of the transfer rollers at any given time, with the exception that for a transfer roller assembly with more than two rollers, a subsequent slice can begin to be applied to first transfer roller 502 at the same time as the slice on second transfer roller 504 is being applied to its slide.

Slide dispenser 332 may be located on the front side of system 300. Slides (not shown) may be manually loaded into slide dispenser 332. Slide dispenser 332 may be a vertical canister mounted directly over slide conveyor 406. Slide dispenser 332 releases one slide (not shown) for each cutting cycle. The release may be managed by system controller 316 and may be triggered by an optical scanner provided in sample block identification area 304 that reads the code on an incoming sample blocks.

In one embodiment, slide dispenser 332 may be provided with a sensor (not shown) for sensing when slide dispenser 332 is running low on slides. This sensor may cause a warning light or other suitable indictor to allow the technician to replenish the slides. If the slide dispenser 332 runs out of slides, system 300 may automatically stop operation.

In another embodiment, other suitable receiving media may be used in place of the slides, such as plastic or film, as discussed above. Typically, the receiving medium will have at least one planar surface.

Slide dispenser 332 may operate as follows. Slide dispenser 332 automatically feeds individual slides for labeling. When system 300 is ready to process a given sample block, the corresponding slides will be sequentially labeled with some or all of this information. System 300 will track each sample block and corresponding slide or slides as they progress.

Activation of slide dispenser 332 may be automatic after a given sample block code is read and entered, or it may be under the manual control of the technician. The number of slides prepared for a given sample block may be determined from an item in the sample block code or it may be manually entered or altered by an technician.

After a tissue sample is applied to the surface of a slide, the slides advance to the end of slide conveyor 406 and may be indexed 90 degrees incrementally onto the slide accumulation conveyor. The slides index based on the ongoing process cycle where each time a process is finished and tissue sample from second transfer roller 504 applied to the surface of a corresponding slide, the accumulation exit conveyor indexes once. The finished slides can be manually picked up as they exit or an accumulating extension can be added to the exit conveyor to increase capacity or they can be conveyed to any other type of unit—for example, a dryer.

The slide accumulation conveyor may have a final code scanner (not shown) which checks the slide code sequence and automatically matches it with the sample block order of process and records it as complete. The technician may have the ability to manually override the cycle of the slide accumulation conveyor.

Sample block exit chute 318 is provided for the sample block to be released into when the requested or requisite number of histologic grade slices have been achieved. The sample block is released into exit chute 318 in the sequence in which they are processed.

As discussed in the background, microtomes generally operate with a vertical orientation. That is, once the sample block, is locked into the microtome's clamp and orientated by the technician to achieve the best working surface orientation, the slicing process (sample block relative to razor blade) is vertical. The present invention, however, may operate with the sample block having either a vertical or a horizontal orientation. Having a horizontal orientation yields several benefits, including the fact that sample blocks enter system 300 in exactly the same way as for the vertical version. However, once within the clamping series they are be shifted horizontally with the sample block's working surface oriented upwards. The slicing to depth and subsequent slices of the actual samples would also be horizontal with the sample block below and parallel to the blade assembly above.

With a horizontal orientation, the transfer roller mechanism will not need to reorientate the sample slices from a generally vertical to a horizontal plane. Their purpose is solely to move the sample slice from the sample block's working surface in a horizontal plane directly onto a slide. This contrasts to the vertical orientation, where the transfer roller mechanism must also reorient the sample slice from a vertical orientation to a horizontal orientation for the slide.

While the invention has been described in connection with preferred embodiments and examples, it will be understood by those skilled in the art that other variations and modifications of the preferred embodiments described above may be made without departing from the scope of the invention. Other embodiments will be apparent to those skilled in the art from a consideration of the specification or practice of the invention disclosed herein. It is intended that the specification is considered as exemplary only, with the true scope and spirit of the invention being indicated by the following claims.

What is claimed is:

1. An apparatus for applying thin sections of a tissue sample to a receiving medium comprising:
   a blade assembly for slicing thin sections from a tissue sample;
   a plurality of transfer rollers sequentially arranged in tangential proximity to each other, such that said thin section in contact with a surface of one transfer roller will be transferred to the surface of the sequentially successive transfer roller;
   wherein a first sequential transfer roller of said plurality of transfer rollers is oriented in proximity to said blade assembly so that said thin section sliced from said tissue sample will contact the surface of said first sequential transfer roller;
   a receiving medium disposed in tangential proximity to a final sequential transfer roller of said plurality of transfer rollers so that said thin section on the surface of said final sequential transfer roller will be transferred to said receiving medium in a substantially smooth and flat configuration;
   a first blade assembly for slicing said tissue sample to expose a working surface; and
   a second blade assembly for producing said thin sections.

2. The apparatus of claim 1, wherein one or more of said first and second blade assemblies comprises:
   a blade supply canister for providing a continuous blade of a predetermined length; and
   wherein said continuous blade is advanced from said blade supply canister at predetermined intervals.

3. An apparatus for automatically producing tissue slides from a tissue sample within a sample block:
   a holding assembly for manipulating said sample block;
   a blade assembly for slicing thin sections from said sample block;
   a transfer roller mechanism for transferring said thin section in contact with a surface of a transfer roller to a receiving medium;
   a controller; and
   an optical imaging system for locating said tissue sample within said sample block;
   wherein said controller determines an optimum orientation of said sample block with respect to said blade assembly.

4. An apparatus for automatically producing tissue slides from a tissue sample within a sample block comprising:
   a holding assembly for manipulating said sample block;
   a blade assembly for slicing thin sections from said sample block;
   a blade supply canister for providing a continuous blade of a predetermined length;
   a transfer roller mechanism for transferring said thin section in contact with a surface of a transfer roller to a receiving medium; and
   a controller;
   wherein said continuous blade is advanced from said blade supply canister at predetermined intervals.

* * * * *

UNITED STATES PATENT AND TRADEMARK OFFICE
CERTIFICATE OF CORRECTION

PATENT NO. : 7,600,457 B2 Page 1 of 1
APPLICATION NO. : 10/091173
DATED : October 13, 2009
INVENTOR(S) : Voneiff et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 760 days.

Signed and Sealed this

Fifth Day of October, 2010

David J. Kappos
*Director of the United States Patent and Trademark Office*